United States Patent
Krauth et al.

(10) Patent No.: US 7,253,904 B2
(45) Date of Patent: Aug. 7, 2007

(54) METHOD AND DEVICE FOR IN-LINE MEASUREMENT OF CHARACTERISTICS OF THE SURFACE COATING OF A METALLURGY PRODUCT

(75) Inventors: Pierre-Jean Krauth, Mondelange (FR); Marco Bini, Madrid (ES)

(73) Assignee: Usinor (FR)

( * ) Notice: Subject to any disclaimer, the term of this patent is extended or adjusted under 35 U.S.C. 154(b) by 0 days.

(21) Appl. No.: 10/522,374

(22) PCT Filed: Jul. 29, 2003

(86) PCT No.: PCT/FR03/02388

§ 371 (c)(1),
(2), (4) Date: Sep. 26, 2005

(87) PCT Pub. No.: WO2004/013619

PCT Pub. Date: Feb. 12, 2004

(65) Prior Publication Data

US 2006/0102831 A1     May 18, 2006

(30) Foreign Application Priority Data

Aug. 1, 2002     (FR) .................................. 02 09845

(51) Int. Cl.
*G01N 21/55*     (2006.01)
*G01N 21/86*     (2006.01)
*G02B 26/00*     (2006.01)

(52) U.S. Cl. ............. 356/445; 250/227.26; 250/559.16

(58) Field of Classification Search ........... 250/227.11, 250/227.26, 559.16; 356/445, 446
See application file for complete search history.

(56) References Cited

U.S. PATENT DOCUMENTS 3,827,963 A     8/1974   Callahan (Continued)

FOREIGN PATENT DOCUMENTS

| CH | 663 473 A5 | 12/1987 |
|---|---|---|
| EP | 0 743 505 A2 | 11/1996 |
| EP | 1 134 578 A1 | 9/2001 |
| JP | 58210159 | 12/1983 |
| JP | 05059518 | 3/1993 |

OTHER PUBLICATIONS

Article entitled "De la mesure de laboratoire a la mesure en ligne et en continu des proprietes radiatives des toles", By Krauth et al., Cahiers d'informations techniques de la revue de metallurgie, revue de metallurgie, Paris, France, vol. 95, No. 6, Jun. 1, 1998, pp. 809-821.

*Primary Examiner*—Thanh X. Luu
*Assistant Examiner*—Brian J. Livedalen
(74) *Attorney, Agent, or Firm*—Bachman & LaPointe

(57) ABSTRACT

To measure the characteristics of the surface coating of a moving metal strip, such as the alliation level of a coating including zinc and iron, the product is exposed to the radiation of a radiative source with a predetermined wavelength directed orthogonally to the surface of the product and the energy reflected by the surface is measured also in a direction orthogonal to the surface so as to overcome reflectivity variations due to the morphological characteristics of the surface and these operations are performed with the help of off-the-shelf optical fibres previously stripped at their free ends of their normal optical focusing accessories so that they can be brought as near to each other as possible and placed parallel to each other.

6 Claims, 2 Drawing Sheets

U.S. PATENT DOCUMENTS

| | | |
|---|---|---|
| 4,278,353 A | 7/1981 | Ostermayer, Jr. |
| 4,886,366 A | 12/1989 | Kogure |
| 4,917,500 A * | 4/1990 | Lugos ........................ 356/406 |
| 5,894,122 A * | 4/1999 | Tomita ........................ 250/234 |
| 6,137,583 A | 10/2000 | Kim et al. |
| 6,222,620 B1 | 4/2001 | Jung et al. |
| 6,597,185 B1 * | 7/2003 | Talanov et al. ............. 324/638 |
| 2003/0142309 A1 * | 7/2003 | Kuebler et al. ............. 356/338 |

* cited by examiner

METHOD AND DEVICE FOR IN-LINE MEASUREMENT OF CHARACTERISTICS OF THE SURFACE COATING OF A METALLURGY PRODUCT

BACKGROUND OF THE INVENTION

The present invention relates to determining the characteristics of a metallurgical product surface coating, in particular in-line, during the feed of the said product during manufacture. It more especially concerns the determining of galvanisation coating characteristics on steel strips in particular of type known under the trade name of GALVALLIA® sheets.

It is recalled here that these sheets are galvanised strips which are submitted to a heat treatment called alliation the aim of which is to provide these strips with improved surface characteristics for example allowing better paint adhesion or offering better stampability.

This alliation treatment is a heat treatment performed on the galvanised strip in an alliation tower with continuous galvanised strip feed. The object of the heat treatment is to ensure diffusion of the iron in the underlayer towards the surface to attain the objectives mentioned above. Typically, the alliation percentage is around 10% in iron concentration in relation to the zinc.

However, at present, the required alliation level, that is the relative extent of this diffusion, varies considerably from one user of the said strips to another and it is therefore important to be able to ensure during manufacture a continuous check of the alliation level. To meet the requests of the customers using the said coated strips, it is therefore necessary to modify during manufacture the adjustment parameters of the installation which performs the alliation heat treatment, that is, mainly the treatment temperature and time.

At present, no system can check in real time and in-line that the GALVALLIA® surface characteristics are those required. Indeed, it is known that alliation causes significant modifications to the surface properties in physicochemical and microgeometrical terms. At present, the alliation level is determined only in laboratory by measuring powdering, iron content or again by metallographical analysis enabling the coating surface crystals to be characterised.

Moreover, to obtain an evaluation as accurate as possible of the surface alliation, it is also necessary to overcome, during the measurement, morphological variations, such as micro-roughness or equivalent geometrical characteristics to ensure sensitivity only to the physicochemical variations of the surface. These physicochemical variations of the extreme surface in fact reflect the migration of the iron atoms of the coating to the extreme surface, which migration corresponds to the alliation level of the product.

As these checks are deferred in relation to production, defects can appear on the strips, such as, for example, powdering or separation of the coating due to an excessive alliation level.

SUMMARY OF THE INVENTION

It is an object of the present invention to especially solve these problems and propose an in-line check of the alliation levels of the surfaces to be able to guarantee an homogeneous and reproducible product and to ensure control of the alliation tower. Its object is, in particular, to limit defects occurring on these strips, such powdering or separation of the coating, and to ensure a homogeneous and reproducible product, especially by avoiding or, at least, reducing the transient underalliation or overalliation zones, that is, zones where the alliation level is uncertain due to voluntary changes in the parameters of the process the check of which cannot be conducted fast enough. More generally, the object of the invention is to allow in-line determination of the surface characteristics of a strip coating liable to vary according to the physicochemical characteristics of the said coating.

With these targets in mind, the subject of the invention is first of all a process for measuring the characteristics of a metallurgical product surface coating, in particular in-line during the feed of the said product during manufacture, wherein, with the object of exposing a zone of the surface of the said product to incident radiation directed orthogonally to the said surface and then of measuring, also in a direction orthogonal to the surface, the energy of the radiation reflected by the exposed zone, the said exposure zone is illuminated by means of a lighting optical fibre connected to an incident radiation emission source with a predetermined wavelength and the reflected radiation is measured by means of a measuring optical fibre connected to a sensor, the free ends of the two optical fibres being stripped and held in the immediate vicinity of each other and parallel to each other.

The invention exploits the fact therefore that the modifications in the surface properties due to modifications in the physicochemical characteristics of the coating are reflected by variations in the reflection properties of the said surface. Moreover, the configuration according to which both the lighting and the observation of the reflected radiation are performed orthogonally to the surface means that the invention is sensitive only to the physicochemical variations of the surface by overcoming the morphological variations. Therefore, the results expected from the measurement by the implementation of the invention will only be attained if this orthogonality is respected and if the two optical fibres concerned, radiation input fibre and return fibre, are very close to each other in their terminal portions with respect to the surface of the product. This is achieved in compliance with the invention by off-the-shelf optical fibres the free ends of which are previously stripped, that is, their usual cumbersome optical focusing accessories are removed to conserve only the fibre itself in stripped form.

The free ends of the two optical fibres can then be held in the immediate vicinity of the surface, typically, for example, at a distance of around 10 to 50 mm from the surface and parallel to each other. This arrangement avoids the use of any other optical focusing systems whilst enabling, thanks to the small section of the optical fibres used (generally around 0.1 mm) and due to the fact that the fibres can be brought close to each other (maximum centre distance also around 0.1 mm), measurement almost exactly in the illuminated zone and with an orientation normal to the surface both for the lighting and for the measurement as will be seen better below.

For the application, especially targeted by the invention, consisting in measuring the alliation percentage of GALVALLIA®, the higher the reflected flux, the lower the alliation percentage as it is the zinc in the coating which produces a higher reflection than the iron.

The information obtained in real time from this measurement can then be used as a parameter to control the alliation tower and also be exploited for quality control to guarantee for the customers the alliation properties of the complete reel delivered.

Preferentially, the radiation used is located in the near infrared range, more particularly with a wavelength of around 830 nm. Indeed, this radiation range was found, after tests conducted by the inventors, to be optimum for measurement sensitivity, taking into account, among other things, radiation sources in current usage such as, for example, a laser diode working at this wavelength.

According to an additional advantageous arrangement, the reflected radiation is also measured in one or more directions oblique to the surface, for example from 0 to 300 from the normal of the surface, which allows the energy diffused by the said surface to be evaluated and additional information to be obtained on the alliation level or on other surface characteristics such as, for example, microgeometrical characteristics which can also be possibly correlated with the direct reflection measurement to give additional information on the general characteristics of the coating.

Measuring the reflected radiation in one or several directions nonorthogonal to the surface itself provides an evaluation of the alliation level as, independent of the morphological characteristics such as micro-roughness or similar, a link was observed between the diffusion along certain angles of reflection and the alliation level, the higher the alliation level, the more the reflected radiation is diffuse. Thus, the comparison between the intensity of the reflected radiation in a direction inclined in relation to the surface and that of the radiation reflected perpendicularly to this surface alone allows the extent of the alliation to be evaluated as will be seen below.

The subject of the invention is also a device to implement the process defined above wherein it includes a measuring head with a front surface intended to be placed opposite the surface of the product to be inspected and including a lighting optical fibre and a measuring optical fibre, these two optical fibres each having, at the front face of the head, a free stripped end so that the corresponding terminal portions of the said fibres are arranged parallel and as near as possible to each other, the other end of the lighting optical fibre being, moreover, connected to a light radiation source and the other end of the measuring optical fibre being connected to a sensor, the device including in addition means for processing the signal supplied by the said sensor to determine the intensity of the radiation which is transmitted to it by the measuring optical fibre.

According to other preferential arrangements of the invention:

the device includes a distance sensor to permanently control or measure the distance between the ends of the optical fibres and the surface of the product, the measuring head includes at least an additional optical fibre connected to a specific sensor, the end part of which is positioned obliquely in relation to the end portion of the lighting optical fire. The orientations of the various fibres will be determined also so that their directions will be convergent onto the same surface zone illuminated by the lighting fibre, the radiation source is a laser diode with an emission wavelength of around 830 nm.

BRIEF DESCRIPTION OF THE DRAWINGS

The invention will be more readily understood on reading the following description relevant to in-line measurement of the alliation level of GALVALLIA® type sheets with reference to the accompanying drawings, in which.

DETAILED DESCRIPTION OF THE PREFERRED EMBODIMENT(S)

Figure 1:
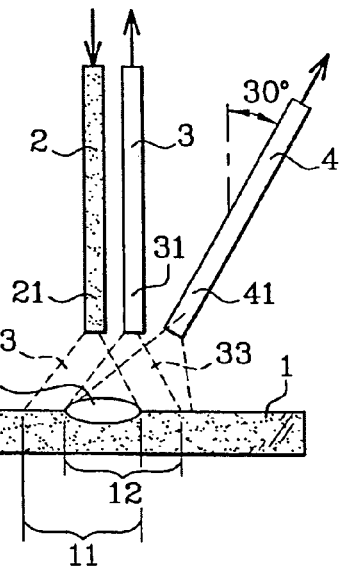
FIG. 1 is a schematic diagram of the measurement principles.

The diagram of FIG. 1 represents a moving steel strip, where zone 11 of its surface 1 is illuminated by infrared radiation 23 from end 21 of a lighting optical fibre 2 held perpendicular to the surface of the strip. A second optical fibre 3, parallel to the lighting fibre 2 and in its immediate vicinity, has its end 31 located at same level as that of the first fibre and captures the reflected radiation 33 supplied by the lighting optical fibre and reflected by the strip.

In fact, due to the unavoidable minimum distance between the axes of the two fibres, even if reduced to a minimum by previously stripping the free end of each fibre, the surface zone 12 seen by the measuring optical fibre 3 is not exactly the lighted zone 11 but, due to the fact that this distance is very small and on account of the natural formation of a diffusion cone 23 from the ends of the fibres, there is a relatively high overlap area 13 of the zones respectively lighted and observed enabling the radiation captured by the measuring fibre 3 to be compared to the complete radiation from the lighting fibre 2 and reflected perpendicularly to surface 1.

FIG. 1 also shows advantageously the presence of a third optical fibre 4 the end 41 of which is inclined by around 300 from the vertical in relation to the first two fibres the observation zone of which is more or less the same as that of the measuring fibre 3.

Figure 2:
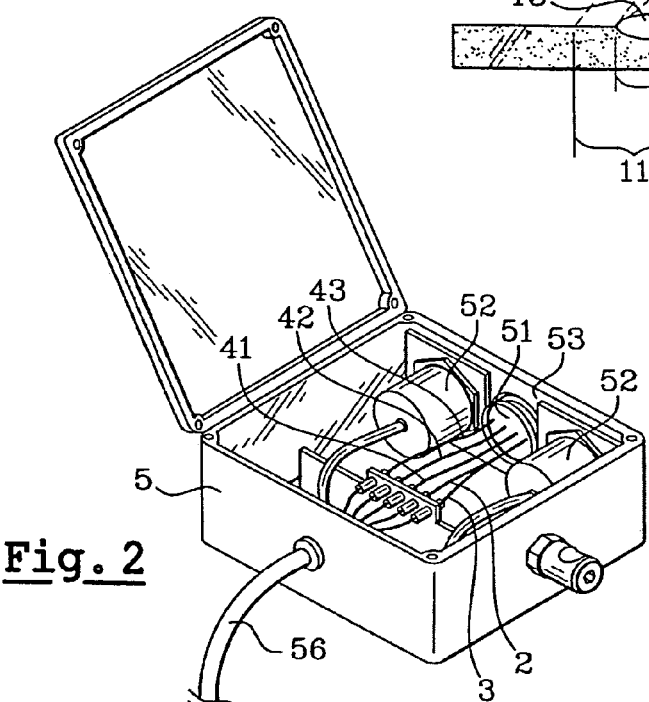
FIG. 2 is a schematic view of the device.

FIG. 2 shows an embodiment example of the device in the form of a case 5 containing a measuring head 51 and two contactless distance sensors 52, of a known type, arranged on a given wall 53 of the case which will be placed when in use at a distance of several tens of millimeters from the surface of the inspected strip.

Figure 3:
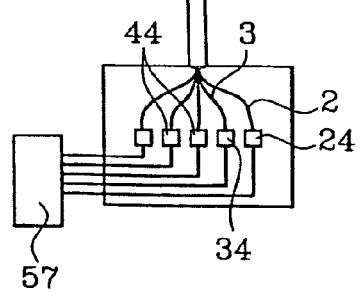
FIG. 3 is a cross-sectional view of the measuring head.

The measuring head 51, a cross-sectional view of which is shown on FIG. 3, includes a cylindrically-shaped body 54 which mainly includes a front wall 55 in which several holes 61 to 64 are drilled intended to accommodate the ends of the various optical fibres of the system. The first one 61 of these holes is perpendicular to the outer surface of the front wall 55 and is shaped so as to simultaneously accommodate the lighting optical fibre 2 and the measuring fibre 3. The three other holes, 62, 63, 64, are oriented along increasing angles in relation to the direction of the first hole, that is, for example, 10, 20 and 300, and their directions are converging and they each accommodate the end of an additional optical fibre, respectively 41, 42, 43.

As shown on FIG. 2, all the fibres, 2, 3, 41, 42, 43, are grouped within the same bundle 56 which extends from the case 5. The lighting optical fibre 2 is connected to an infrared radiation source, such as a laser diode 24, and the other fibres, 3, 41, 42, 43, are connected to sensors 34, 44 respectively, of a known, type for measuring the intensity of the reflected radiation, the signals from the sensors being processed by a processing unit 57.

Figure 4:
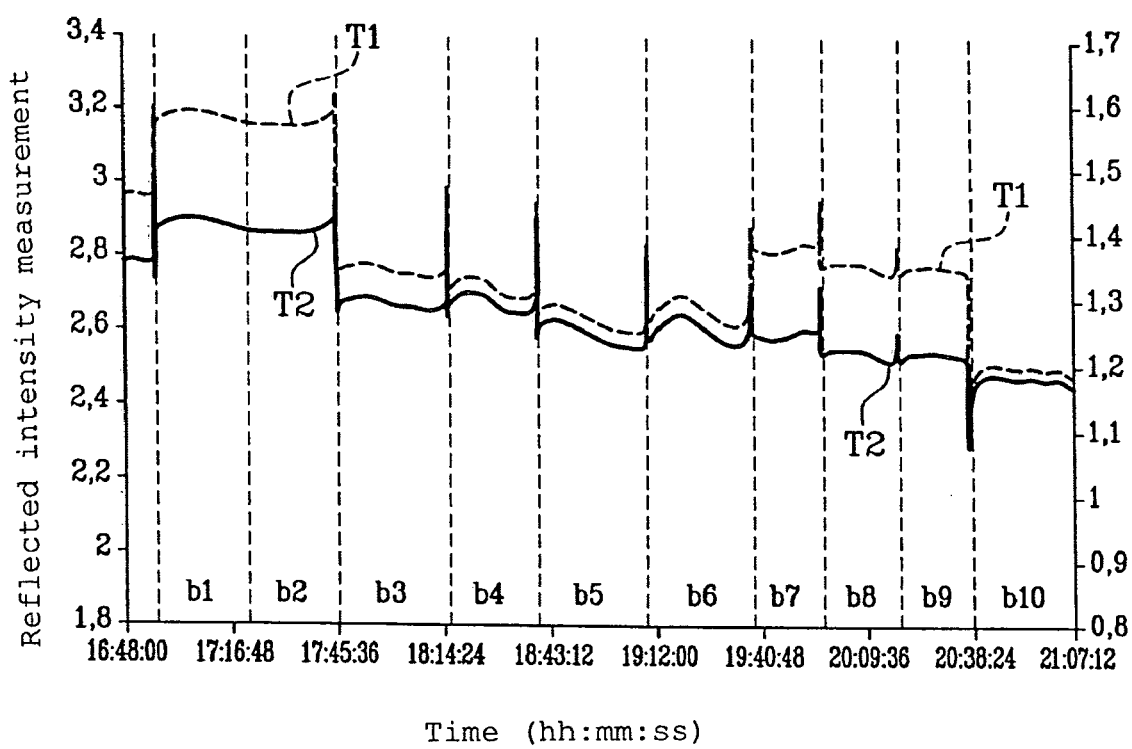
FIG. 4 is a graph illustrating the results of a set of measurements on GALVALLIA® sheet reels showing various alliation levels.

The graph on FIG. 4 shows the results of measurements made by means of the device described above on a strip fed through the invention. In fact, in the example shown, the measurements were made during the feedthrough of 10 strip reels, identified b1 to b10, with different alliation percentages.

The first two reels, b1 and b2, have an alliation percentage of around 10% and powdering, measured under standardised test conditions, of 3 to 4 grams/m² (weight of powder separated from the strip under test conditions).

Reels b3 to b6 have an alliation percentage of 12% and powdering of 5 to 6 g/m². Reels b7 to b9 have an alliation percentage of 11% and powdering of 4 g/m². Reel b10 has an alliation percentage of 13% and powdering of 7 g/m².

The two plots shown correspond respectively to the reflected intensity versus time measurements, that is versus the length of the sheet strip being fed through the alliation oven. The top plot T1 on the graph represents the radiation intensity captured by the measuring optical fibre 3 and the bottom plot T2 represents the radiation intensity captured by the optical fibre 43 which passes through hole 64 inclined at 30°.

It can be clearly seen that the lower the alliation percentage (reels 1 and 2), the higher the intensity of the reflected signal which correctly corresponds to a high reflectivity due to the low proportion of iron in the zinc of the coating and, conversely, if the alliation rate is high (reel 10), the reflected intensity is lower, illustrating loss of reflectivity due to the higher content of surface iron.

It can also be seen that the difference between plots T1 and T2 is clearly higher for reels b1 and b2 or b7 to b9 than for reels b3 to b6 and b10 which also illustrates the fact that the dispersion of the reflected radiation is higher for low alliation levels when the quantity of surface iron is lower.

The invention is not limited, in the embodiment of the device or of the measuring head or in the implementation of the process, to the example described above. In particular, the infrared laser diode can be replaced by other radiation sources with wavelengths suitable to the surface to be checked. Also, products other than GALVALLIA® can be checked in a similar manner and also the signals delivered by various sensors, connected to the optical fibres with different inclinations, can be analysed to obtain other information, in particular concerning the morphological characteristics of the surface.

What is claimed is:

1. Process for determining the alliation percentage of a galvanized steel strip product in-line during a feed of the product during manufacture, comprising the steps of exposing a zone of a surface of the product to incident radiation directed orthogonally to the surface and measuring, also in a direction orthogonal to the surface, the radiation energy reflected by the exposed zone, said exposing step comprising illuminating said zone by a lighting optical fibre having a stripped free end and connected to an incident radiation emission source with a predetermined wavelength and said measuring step comprising measuring the reflected radiation by means of a measuring optical fibre having a stripped free end and connected to a sensor, and wherein the process includes holding the stripped free ends in the immediate vicinity of each other and parallel to each other and perpendicularly to the surface of the product during said exposing and measuring steps, wherein the measuring step comprises also measuring the reflected radiation in at least one direction oblique to the surface of the product, at an angle between 10 and 30 degrees from the perpendicular to the surface, to evaluate the energy diffused by the illuminated zone.

2. The process according to claim 1, wherein said holding step comprises holding the stripped free ends of the optical fibres at a distance from the surface of the product of between 5 and 50 mm.

3. The process according to claim 1, wherein the radiation used is located in a near infrared range with a wavelength of 830 nm.

4. Device for determining the alliation percentage of a galvanized steel strip in-line during a feed of the product during manufacture, said device including a measuring head with a front surface placed opposite a surface of the product and including a lighting optical fibre and a measuring optical fibre, the two optical fibres each having, at a front face of the head, a free stripped end and so that corresponding terminal portions of the fibres are arranged parallel and as close to each other as possible and perpendicular to the surface of the product, another end of the lighting optical fibre being connected to a light radiation source and another end of the measuring optical fibre being connected to a sensor, wherein the measuring head includes an additional optical fibre connected to a specific sensor and having a free end part of which is oriented obliquely in relation to the free end portion of the lighting optical fibre at an angle between 10 and 30 degrees, and the device including in addition means for processing a signal supplied by the sensor for determining intensity of the radiation which is transmitted to the sensor by the measuring optical fibre.

5. The device according to claim 4, further including a distance sensor to permanently measure a distance between the free stripped ends of the optical fibres and the surface of the product.

6. The device according to claim 4, wherein the radiation source is a laser diode having an emission wavelength of around 830 nm.

* * * * *